US010438347B2

(12) United States Patent
Enzmann et al.

(10) Patent No.: US 10,438,347 B2
(45) Date of Patent: Oct. 8, 2019

(54) AUTOMATED QUALITY CONTROL OF DIAGNOSTIC RADIOLOGY

(71) Applicant: THE REGENTS OF THE UNIVERSITY OF CALIFORNIA, Oakland, CA (US)

(72) Inventors: Dieter Enzmann, Beverly Hills, CA (US); William Hsu, Westlake Village, CA (US); Corey W. Arnold, Los Angeles, CA (US); Alex A. T. Bui, Los Angeles, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 4 days.

(21) Appl. No.: 15/254,798

(22) Filed: Sep. 1, 2016

(65) Prior Publication Data
US 2017/0053074 A1 Feb. 23, 2017

Related U.S. Application Data

(63) Continuation of application No. PCT/US2015/018825, filed on Mar. 4, 2015.
(Continued)

(51) Int. Cl.
*G06K 9/00* (2006.01)
*G06T 7/00* (2017.01)
(Continued)

(52) U.S. Cl.
CPC ......... *G06T 7/0012* (2013.01); *G06Q 10/103* (2013.01); *G06Q 50/24* (2013.01);
(Continued)

(58) Field of Classification Search
None
See application file for complete search history.

(56) References Cited

U.S. PATENT DOCUMENTS 5,652,842 A 7/1997 Siegrist, Jr. et al.
6,058,322 A * 5/2000 Nishikawa ............ G06T 7/0012
128/925
(Continued)

FOREIGN PATENT DOCUMENTS

WO 2007-089686 A2 8/2007
WO WO 2011063529 A1 * 6/2011 .......... G06F 19/321
WO 2013-175683 A1 11/2013

OTHER PUBLICATIONS

Van Stralen, Karlijn J., et al. "Diagnostic methods I: sensitivity, specificity, and other measures of accuracy." Kidney international 75.12 (2009): 1257-1263. (Year: 2009).*
(Continued)

*Primary Examiner* — Samah A Beg
(74) *Attorney, Agent, or Firm* — O'Banion & Ritchey LLP; John P. O'Banion (57) ABSTRACT

A system is disclosed using a data-driven approach to objectively measure the diagnostic accuracy and value of diagnostic imaging reports using data captured routinely as part of the electronic health record. The system further utilizes the evaluation of the diagnostic accuracy of individual radiologists (imagers), subspecialty sections, modalities, and entire departments based on a comparison against a "precision diagnosis" rendered by other clinical data sources such as pathology, surgery, laboratory tests, etc.

13 Claims, 5 Drawing Sheets

Related U.S. Application Data (60) Provisional application No. 61/947,563, filed on Mar. 4, 2014.

(51) Int. Cl.
    *G06Q 50/24*       (2012.01)
    *G06Q 10/10*       (2012.01)
    *G16H 15/00*       (2018.01)
    *G16H 10/00*       (2018.01)
    *G16H 80/00*       (2018.01)
    *G16H 40/20*       (2018.01)
    *G06F 19/00*       (2018.01)

(52) U.S. Cl.
CPC .. *G06F 19/321* (2013.01); *G06T 2207/10116* (2013.01); *G06T 2207/30068* (2013.01); *G06T 2207/30096* (2013.01); *G16H 10/00* (2018.01); *G16H 15/00* (2018.01); *G16H 40/20* (2018.01); *G16H 80/00* (2018.01)

(56) References Cited

U.S. PATENT DOCUMENTS

| | | | | |
|---|---|---|---|---|
| 6,669,482 | B1 * | 12/2003 | Shile | G09B 23/286 434/262 |
| 6,920,439 | B1 * | 7/2005 | Love | G06N 3/0472 706/20 |
| 8,082,172 | B2 | 12/2011 | Chao et al. | |
| 9,383,347 | B2 * | 7/2016 | Marugame | G01N 33/4833 |
| 2006/0173266 | A1 * | 8/2006 | Pawluczyk | G01N 21/64 600/407 |
| 2006/0274145 | A1 * | 12/2006 | Reiner | G06F 17/3028 348/62 |
| 2007/0179811 | A1 * | 8/2007 | Reiner | G06F 19/321 705/2 |
| 2007/0240038 | A1 * | 10/2007 | Rundell | G06F 19/327 715/210 |
| 2008/0312963 | A1 * | 12/2008 | Reiner | G06F 19/327 705/2 |
| 2009/0006132 | A1 * | 1/2009 | Avinash | G16H 10/60 705/3 |
| 2009/0018867 | A1 * | 1/2009 | Reiner | G06F 3/04883 705/2 |
| 2009/0060297 | A1 * | 3/2009 | Penn | G06T 7/0012 382/128 |
| 2010/0093108 | A1 * | 4/2010 | Khattar | C12Q 1/6886 436/518 |
| 2010/0145720 | A1 * | 6/2010 | Reiner | G06F 19/3443 705/2 |
| 2010/0174994 | A1 * | 7/2010 | Marx | G06F 19/321 715/738 |
| 2010/0235184 | A1 * | 9/2010 | Firminger | G06F 19/3418 705/2 |
| 2011/0123073 | A1 * | 5/2011 | Gustafson | G06F 19/321 382/128 |
| 2011/0218815 | A1 * | 9/2011 | Reiner | G06Q 50/22 705/2 |
| 2011/0270623 | A1 * | 11/2011 | Reiner | G06F 19/321 705/2 |
| 2011/0276346 | A1 * | 11/2011 | Reiner | G06F 19/327 705/3 |
| 2012/0066031 | A1 | 3/2012 | Chao et al. | |
| 2012/0203575 | A1 * | 8/2012 | Tulipano | G06F 19/3487 705/3 |
| 2012/0208161 | A1 | 8/2012 | Takata et al. | |
| 2012/0245952 | A1 * | 9/2012 | Halterman | G06F 19/3425 705/2 |
| 2012/0330447 | A1 * | 12/2012 | Gerlach | G01B 11/24 700/95 |
| 2013/0136330 | A1 | 5/2013 | Takagi | |
| 2014/0025390 | A1 * | 1/2014 | Shen | G06Q 50/22 705/2 |
| 2014/0244283 | A1 * | 8/2014 | Smith | G06F 19/327 705/2 |
| 2014/0314292 | A1 * | 10/2014 | Kamen | A61B 6/463 382/131 |
| 2014/0358585 | A1 * | 12/2014 | Reiner | G06F 19/322 705/3 |
| 2015/0081332 | A1 * | 3/2015 | Casper | G06F 19/322 705/3 |
| 2016/0048956 | A1 * | 2/2016 | Bryan | G06T 7/0012 382/128 |
| 2016/0232321 | A1 * | 8/2016 | Silverman | G06F 19/3437 |
| 2016/0235372 | A1 * | 8/2016 | Schneider | A61B 5/0075 |
| 2016/0267226 | A1 * | 9/2016 | Xu | G06F 19/327 |
| 2017/0161625 | A1 * | 6/2017 | Jannson | G06N 7/005 |
| 2017/0228455 | A1 * | 8/2017 | Alter | G06F 17/30675 |
| 2018/0060744 | A1 * | 3/2018 | Achin | G06N 20/00 |

OTHER PUBLICATIONS

Korean Intellectual Property Office (KIPO), International Search Report and Written Opinion, PCT International Application No. PCT/US2015/018825, dated May 29, 2015, pp. 1-13, with claims searched, pp. 14-19.

American College of Radiology, Radpeer user guide radiologist, downloaded from http://www.acr.org/~/media/ACR/Documents/PDF/QualitySafety/Radpeer/User%20Guide%20Radiologist.pdf on Sep. 1, 2016, pp. 1-8.

American College of Radiology, Radpeer user guide admin poc, downloaded from http://www.acr.org/~/media/ACR/Documents/PDF/QualitySafety/Radpeer/User%20Guide%20Admin%20POC.pdf on Sep. 1, 2016, pp. 1-20.

* cited by examiner

Filters

Modality
- ☐ Computed Radiography (CR)
- ☐ Computed Tomography (CT)
- ☐ Laser Surface Scan (LS)
- ☒ Mammography (MG)
- ☐ Magnetic Resonance (MR)
- ☐ Radiographic Imaging (RG)
- ☐ SR Document (SR)
- ☒ Ultrasound (US)

Radiology Assessment
- ☐ 1 - Negative
- ☐ 2 - Benign finding(s)
- ☐ 3 - Probably benign
- ☒ 4 - Suspicious abnormality
- ☒ 4A - Low suspicion
- ☒ 4B - Intermediate suspicion
- ☒ 4C - Moderate suspicion
- ☐ 5 - Highly suggestive
- ☐ 6 - Known biopsy- proven

Biopsy Assessment
- ☒ Benign
- ☒ Malignant

Start Date (mm/dd/yyyy):
01/01/2002

End Date (mm/dd/yyyy):
3/1/2013

AUTOMATED QUALITY CONTROL OF DIAGNOSTIC RADIOLOGY

CROSS-REFERENCE TO RELATED APPLICATIONS

This application is a 35 U.S.C. § 111(a) continuation of PCT international application number PCT/US2015/018825 filed on Mar. 4, 2015, incorporated herein by reference in its entirety, which claims priority to, and the benefit of, U.S. provisional patent application Ser. No. 61/947,563 filed on Mar. 4, 2014, incorporated herein by reference in its entirety. Priority is claimed to each of the foregoing applications.

The above-referenced PCT international application was published as PCT International Publication No. WO 2015/018825 on Sep. 11, 2015, which publication is incorporated herein by reference in its entirety.

STATEMENT REGARDING FEDERALLY SPONSORED RESEARCH OR DEVELOPMENT

Not Applicable

INCORPORATION-BY-REFERENCE OF COMPUTER PROGRAM APPENDIX

Not Applicable

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. § 1.14.

BACKGROUND

1. Technical Field

This description pertains generally to medical diagnostic quality assessment, and more particularly to medical assessment for radiology and pathology.

2. Background Discussion

The changing landscape of healthcare reimbursement and the shift from fee-for-service to value-based reimbursement have underscored the need to objectively assess the value of information that radiologic interpretations provide within the context of a patient's care. Measures of value may come from the accuracy with which a patient's condition is diagnosed to the time saved to reach the appropriate diagnosis. However, previous studies have demonstrated that approximately 4% of radiological interpretations reported during daily practice contain errors.

Furthermore, variability in radiologist interpretations may exceed 45% among radiologists, as evidenced in a study that compared breast recommendations at accredited medical centers. Current tools for reviewing diagnostic accuracy include RADPEER and RadReview, which are online peer-review systems that score clinical performance based on the completeness of findings, interpretation of the findings, and significance of omissions. Nevertheless, several shortcomings are noted: 1) both peer-review systems do not address variability in interpretation, assuming that another radiologists' findings serves as the "gold-standard"; 2) the process is time consuming, resulting in lost productivity; 3) the criteria for grading may not be clearly defined or followed by reviewers; and 4) the assessment is limited to the information available at the time of interpretation, which does not address the broader question of what value the radiologic interpretation has on the patient's outcome.

Accordingly, an object of the present description is a more objective approach to assessing the quality and utility of radiology reports.

BRIEF SUMMARY

An aspect of the present description is an automated approach to assessing the value of radiologic interpretations by comparing radiology findings with diagnoses provided by other clinical data sources (e.g., pathology). The goal of this work is to establish an approach for automatically determining the level of concordance between radiology and other clinical information at multiple levels of granularity from individual radiologists to subspecialty sections, modalities, and the entire department. The system utilizes downstream diagnostic conclusions from other departments, such as pathology and surgery, as "truth" measurements to which the upstream diagnoses generated by radiology are compared.

In one aspect, the system of the present disclosure uses a data-driven approach to objectively measure the diagnostic accuracy and value of diagnostic imaging reports (e.g. radiology) based on a comparison against a "precision diagnosis" rendered by other clinical data sources such as pathology, surgery, laboratory tests, etc. The system further utilizes the evaluation of the diagnostic accuracy of radiologists or any individual who may provide interpretations from diagnostic images (imagers), subspecialty sections, modalities, and entire departments to provide a means for quantitatively assessing differences between imaging-derived interpretations and other clinical information, providing a basis for continuing education and quality improvement.

In one aspect, the system performs an automated mapping between image-based findings and findings from "precision diagnosis" sources, computing the concordance between the two findings. The system allows for real-time or retrospective analysis of imager diagnostic performance (e.g., accuracy of diagnosis, time required until diagnosis) and provides a means for adaptively assigning new cases to imagers based on their performance on past studies.

In one embodiment, the system is realized as an electronic software application that can be incorporated as part of existing radiology information systems. A commercial application may be implemented to integrate the information extraction, comparison, and scoring techniques with the electronic medical record system at an institution.

In one embodiment, the system includes informatics tools to automatically extract, structure, and compare information from the electronic health record to generate relevant metrics such as concordance and time required to reach diagnosis.

In another embodiment, the system includes a scoring algorithm to quantify the value of radiologic interpretation in terms of knowledge added to the process of care, rewarding imagers with specificity in diagnosis and actionable guidance.

One aspect is a web-based interface to visualize the results of the imagers' performance. The interface includes a dashboard that allows users to generate custom reports based on several criteria: individual imagers, imaging modality, BI-RADS score (in the case of breast imaging, but another scoring system can be used), and date ranges. Once user-defined criteria have been selected, the system automatically retrieves information for the matching set of patients. Radiologic and pathologic findings for each individual are arranged in chronological order, generating a timeline of events. To compute concordance, a strict criterion is used in comparing the imaging exam immediately preceding the pathological result. Laterality and clock face are also considered in the mapping process. Further classification is performed to assign pathological findings to one of three categories: benign, high-risk, and malignant.

Embodiments of the system of the present disclosure may provide one or more of the following advantageous features:

1. Automatic detection of diagnostic statements from natural language used in radiology reports.

2. Classification of diagnostic statements into general and specific disease categories.

3. A metric for assessing concordance between image-derived diagnostic finding and "precision diagnosis" provided by another clinical data source.

4. A real-time, data-driven platform for understanding radiology diagnostic accuracy and concordance between imaging and another clinical data source.

5. A means for characterizing the information content of diagnostic reports produced by imagers, characterizing diagnostic accuracy, and presence of actionable information for individuals to entire departments.

Further aspects of the technology will be brought out in the following portions of the specification, wherein the detailed description is for the purpose of fully disclosing preferred embodiments of the technology without placing limitations thereon.

BRIEF DESCRIPTION OF THE SEVERAL VIEWS OF THE DRAWING(S)

The technology described herein will be more fully understood by reference to the following drawings which are for illustrative purposes only.

DETAILED DESCRIPTION

The system and methods detailed below objectively assess diagnostic accuracy based on comparison with findings from other clinical sources such as pathology ("precision diagnosis") rather than an interpretation rendered by peers.

The system detailed below is particularly directed to evaluation of the concordance between breast biopsy recommendations reported using Breast Imaging-Reporting and Data System (BI-RADS) and actual pathological diagnosis from those individuals who undergo a biopsy. The system integrates real-time data from clinical systems as inputs to automatically generate a dashboard that reports information about the concordance rates between as-signed BIRADS scores and pathology assessments. The system routinely retrieves radiology exam information for breast imaging such as modality, exam and interpretation dates, signing radiologist, BIRADS assessment, and full-text report. For the same patients, the system also retrieves information from the pathology laboratory information system such as specimen description, date of completion, and final diagnosis. Computed metrics include overall concordance rate, time between imaging and biopsy, number of imaging studies required prior to diagnosis, accuracy of diagnosis for individual radiologists and modalities, and changes in concordance over time.

While the system and methods are described in the context of breast imaging, which is a relatively straightforward domain given the existence of a standardized scoring system, it is appreciated that the systems and methods described herein are generalizable to other diagnostic imaging areas. For example, the specificity by which findings are described (e.g., the presence of an abnormality versus the severity of an abnormality) may use different, specialized scoring algorithms. Some exemplary uses may comprise other cancer domains such as prostate and lung. The use of a standardized scoring system such as BIRADS (e.g., PI-RADS in the case of prostate) would assist in generating an objective scoring metric. The information derived from the system and methods of the present disclosure may be useful in assessing the value of imaging information and improving the quality of information that radiology contributes to the patient's process of care.

Figure 1:
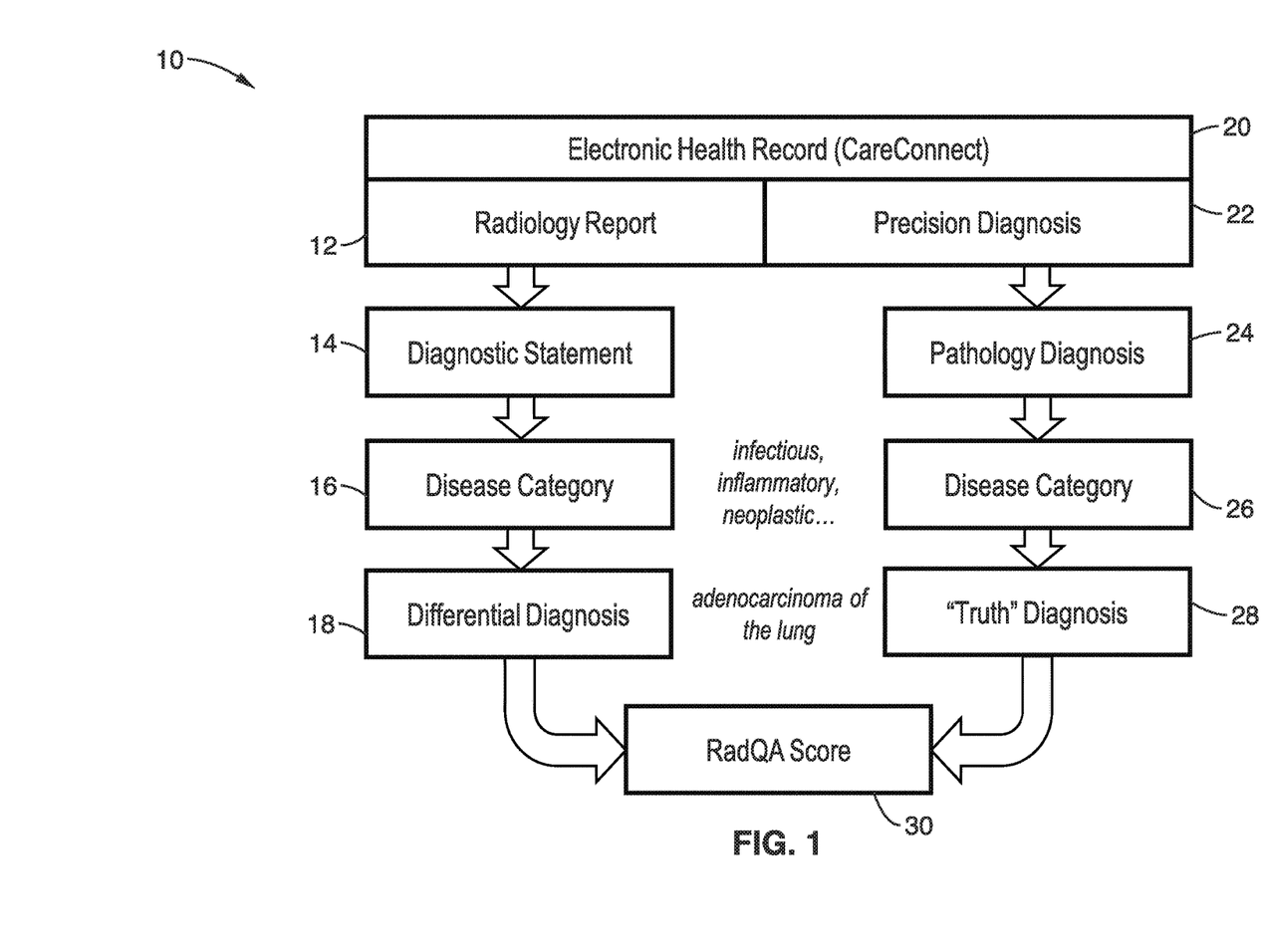
FIG. 1 is a schematic flow diagram of a quality assessment method in accordance with the present disclosure.
Figure 2:
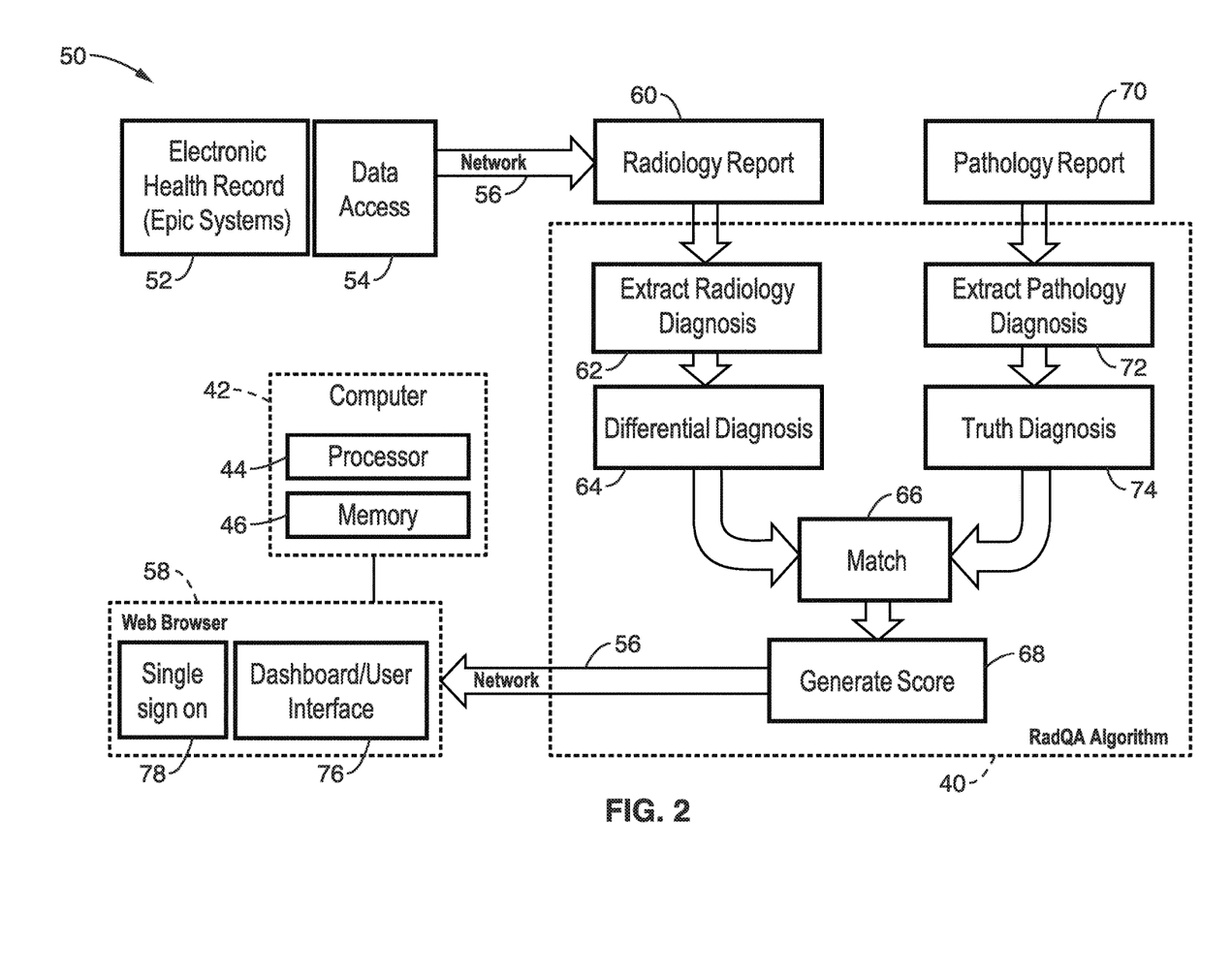
FIG. 2 is a schematic diagram of a quality assessment system in accordance with the present disclosure.

Referring to the data-driven quality assessment quality flow process 10 shown in the flow diagram of FIG. 1 and the system 50 architecture diagram of FIG. 2, the methods and systems of the technology of the present disclosure utilize a number of pre-existing components within the healthcare system. The data-driven approach of the present disclosure ideally comprises a fully functional electronic health record system that contains patient demographics, radiology, and pathology report information in a machine parse-able, textual format. This information can be in free-text. Structured information such as date of exams and exam description are beneficial to match appropriate radiology and pathology exams. Exemplary systems include Epic System's medical record system, a local implementation which is called Care-Connect.

For the process flow 10 of FIG. 1, electronic health records in the form of radiology reports 12 and precision diagnoses 22 are part of the electronic health record dataset 20. From the radiology report 12, the process 10 extracts data relating to the diagnostic statement 14, disease category 16, and differential diagnosis 18. Data is also extracted from the precision diagnosis 22 to generate the pathology diagnosis 24, disease category 26 and "truth" diagnosis 28. The "truth" diagnosis 28 and differential diagnosis 18 are then used to generate score 30.

Referring to FIG. 2, the system architecture 50 also includes compatibility with existing data access modules 54. Given that electronic health record systems contain protected health information within the health records 52, federal regulations require that the information be maintained in a secure manner. As such, medical record systems typically do not permit direct access to the underlying database. The data access module 54 acts as the gatekeeper to patients' medical data by authenticating applications and auditing all information requests from the medical record 52. System 50 is configured for retrieval of only patient information that is solely related to the radiological exam (patient id, exam description, exam date, study result, signed by, and status) and pathological exam (patient id, result date/time, test name, specimen description, result information, component results, and status). In one exemplary configuration, a database reporting tool called Clarity and an infrastructure called xDR (enterprise data repository) may be used as the data access module 54 to access information in the patient record 52 for clinical analytics.

With respect to radiology reports 60, each institution may likely have its own standards and formats for radiology reports. At most institutions, radiology reports are semi-structured, free-text documents that are divided into sections and sentences. Sections may be delineated by headings such as "Clinical information", "Technique", "Findings", and "Impressions". The impressions section typically contains information regarding the radiological diagnosis.

Similarly, each institution may have its own format for pathology reports 70. At most institutions, pathology reports are organized by headings with some free-text underneath each heading. For example, one embodiment specifically examines information under the "Final Diagnosis" heading.

Each institution may require users to log into an authentication system before giving access to sensitive information. As such, a single sign-on component 78 may be used to interface with the authentication mechanism (e.g. dashboard 76) at the institution (e.g., Shibboleth). In such embodiment, users would enter a valid username and password before viewing and interacting with the dashboard 58. The interface may preferably be configured to operate over a web browser 58 to interface with the application software 40 via computer 42 over network interface 56 (e.g. Internet). The application software 40 is configured to comprise instructions stored in memory that are executable on a computer 42, server of the like device having a processor 44 and memory 46.

A high level description of the process flow of system 50 and application software 40 is as follows:

For a given patient in the cohort, the software 40 first locates the pathology report (T) 70 that contains the "truth" or "gold standard" diagnosis (TD) 74 for the disease of interest. This is performed via the pathology extraction module 72.

For all diagnostic radiology reports 60 related to the disease of interest preceding T, use informatics tools within the radiology extraction module 62 are used to extract the differential diagnoses (DD) at module 64 and recommendations (R) provided by the radiologist.

At module 66, the truth diagnosis 74 is matched with the differential diagnosis 64, and then a quality assessment score is generated at module 68 by comparing over time the differential diagnoses 64 in DD to the true diagnosis, TD, 74. This score may also be weighted by radiologist recommendations, R.

At radiology extraction module 62, the software 40 first tokenizes the entire document (radiology report 60) into sections and boundaries tokenization on the radiology report using an open-source tool called Apache OpenNLP. Specifically, the document 60 is examined for stop characters (e.g., new line characters, periods, and colons, etc.) that are then used to divide the entire documentation into parts. The section tokenization is performed by writing a series of regular expressions that utilize specific patterns of keywords, capital letters, and symbols such as the colon (e.g., "IMPRESSIONS:") to identify radiology-specific sections.

The sentences are then tokenized under the "Impressions" heading for further analysis. A sentence is identified as longest white space trimmed character sequence between two punctuation marks. These sentences are defined as radiology diagnostic statements.

Similar to the radiology report 60, the free-text pathology report 70 is also divided into sections and sentences at pathology extraction diagnosis module 72. The approach is generally identical to the radiology report 60, except that the section heading patterns will likely vary. Instead of terms such as "Impressions", pathology utilizes terms such as "Final Diagnosis". We tokenize the sentences under the "Final Diagnosis" heading for further analysis. These sentences are defined as pathology diagnostic statements.

In a preferred embodiment, the radiology diagnostic statements identified in the radiology extraction module 62 contain the differential diagnosis 64. These sentences may contain words and phrases such as "infectious", "inflammatory", "neoplastic", "negative", "benign", "suspicious", and "highly suggestive of malignancy." In some domains, such as breast, standardized terms are used (e.g., Breast Imaging, Reporting and Data System, BIRADS) to convey the certainty and severity of a patient having breast cancer.

Preferably, a dictionary lookup method may be implemented to identify sentences that contain the aforementioned terms. First, a large collection of radiology reports are manually reviewed, enumerating words that are related to the aforementioned categories; the result of this process is a collection of terms associated with each category. Given a new sentence, the number of times words in the sentence matches a specific category are then counted. Three outcomes may occur: 1) an exact match, in which the matching category is assigned; 2) some of the words match, in which the category with the most frequency of matching words are assigned; or 3) no terms match, in which the sentence is categorized as "unassignable."

Also associated with a differential diagnosis 64 may be a radiology recommendation (R), which provides actionable information about next steps to the referring physician for the diagnostic process. The QA score 68 can be optionally weighted based on whether the radiologist provides a recommendation and whether the recommendation resulted in a reduced amount of time to confirm the malignancy. The same dictionary lookup method as described previously may be used, yet adapted to recommendation-related terms to identify actionable statements associated with the DD 64. A large number of historical cases are examined to identify recommendation-related terms and to compute the probability of a recommendation leading to a pathological confirmation of a malignancy in the patient within a pre-defined window of time (e.g., within one month of scan).

With respect to the truth diagnosis 74, the pathology diagnostic statement extracted from the pathology extraction module 72 is considered the "truth" or "reference" diagnosis. Typically, pathology diagnoses vary based on domain (e.g., prostate, breast, lung). To categorize pathology diagnosis, a list of possible disease names is generated from a large collection of pathology reports. This process is aided using a coding system, such as the International Classification of Diseases (ICD). Additional information such tumor grade (e.g., based on the appearance and aggressiveness of the tumor) may also be available.

Text matching between phrases in the pathology report to the list of disease terms is then performed. Once matched with a standard disease term, the disease term is classified as either being benign or malignant.

A conditional random field (CRF) model may be trained to perform this task. The training process is as follows: a large set of labeled examples is first provided (e.g., ductal hyperplasia=benign) from a database of physician-reviewed cases. The CRF is a common statistical model for text classification. When a new, unseen case is presented to the CRF, it computes a probability of whether the case is benign or malignant based on a prior probability estimated from previously seen cases. This approach can be generalized to go beyond two classes (benign/malignant): a CRF can also be trained on a large number of categories, as long as those categories are represented in the training set.

To generate the QA score 68 for a given individual or department, the differential diagnosis (DD) 64 is first matched to the appropriate truth diagnosis (TD) 74 at matching module. Two scenarios may occur: 1) an explicit matching occurs, where a pathologist explicitly links the DD and TD by referring to the corresponding radiology report 60 in the pathology report 70; or 2) an implicit matching occurs, where the radiology exam immediately prior to the pathology exam is defined to be matched. To ensure that the radiology DD 64 is matched to the appropriate pathology TD 74 (as a patient may have multiple radiology/pathology exams), contextual information such as the anatomical location and laterality of the image findings should match with the anatomical location and laterality of where the specimen is taken. This information may be drawn from structured fields in the institution's electronic health record.

The QA score is computed by scoring module 68 by examining the proportion of cases where the radiologic categorical assessment matches that of the pathology categorical assessment from matching module 66.

The QA score can be computed at both the individual-level and the department-level via Eq. 1:

$$QA\ Score = \frac{DD \cap TD}{n} \times P(TD|R) \qquad \text{Eq. 1}$$

where DD∩TD represents the number of exams whether DD 64 and TD 74 match, divided by n (total number of pathology exams). The QA score can be optionally weighted by an additional term, P(TD|R), which represents the probability of TD being reached within a predefined time period (e.g., median time between the radiology and pathology exams) given a radiologist's recommendation, R. An individual-level QA score is computed on exams signed by that individual radiologist. A department-level QA score is ideally computed on all exams, regardless of the signing radiologist. Metrics are also generated based on the total number of patients that match user inputted filters described with respect to the dashboard 76: 1) the proportion of patients assigned a specific pathology category; 2) the proportion of patients who underwent a specific type of imaging modality (e.g., magnetic resonance imaging); 3) the frequency of individuals who are assigned a specific radiology category; 4) the average time between matched radiology and pathology exams; and 5) a comparison of an individual radiologist's radiology-pathology score in comparison to the department's average.

Figure 3A:
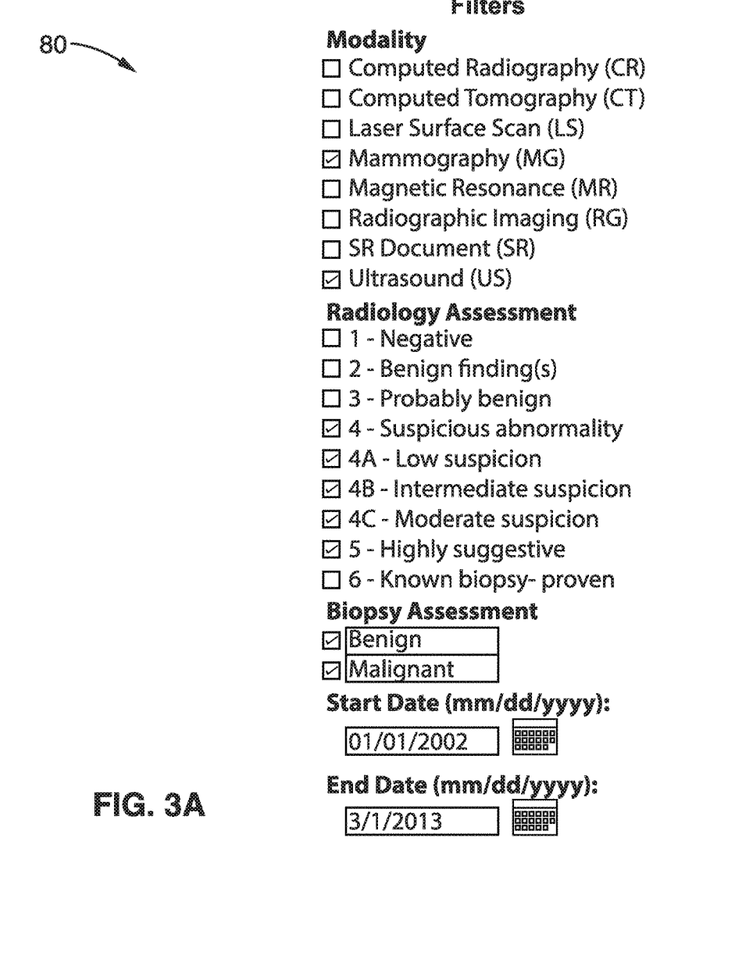
FIG. 3A shows a filtering module of the user interface dashboard in accordance with the present description.
Figure 3B:
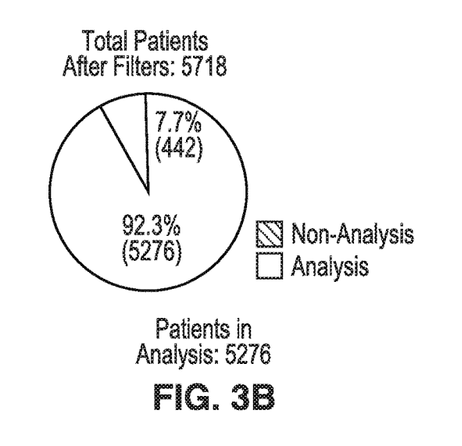
FIG. 3B through FIG. 3G show a series of output visualizations of the user interface dashboard in accordance with the present description.
Figure 3C:
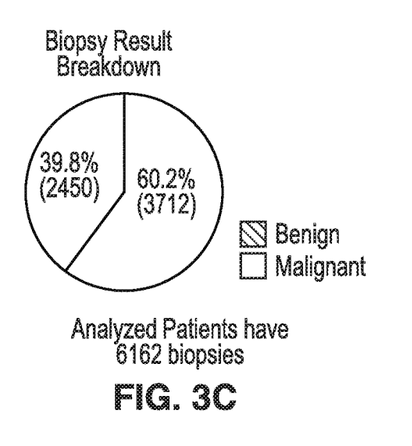
Figure 3D:
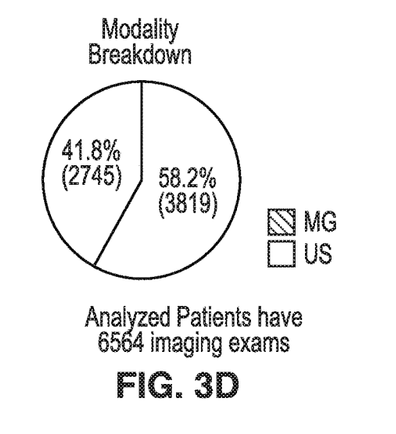
Figure 3E:
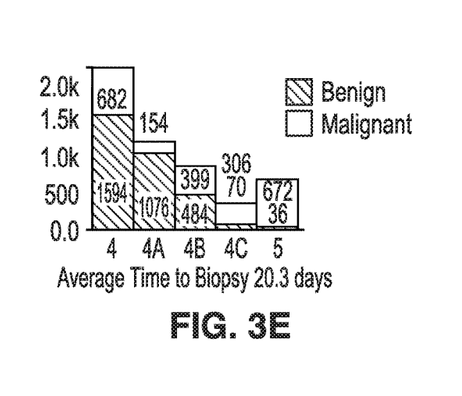
Figure 3F:
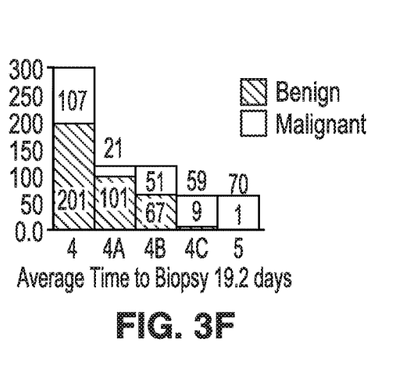
Figure 3G:
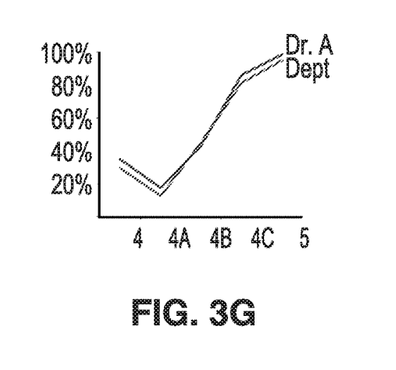

The dashboard 76 preferably provides a set of visualizations (shown in FIG. 3B through FIG. 3G) that summarize the computed scores according to specified filters 80 in FIG. 3A. A user first authenticates into the system 50 by providing a valid username and password through the single sign-on mechanism 78 via browser 58. The username is mapped to the user's full name through the sign-on mechanism 78. This permits the interface 76 to show only statistics relevant to that individual. For instance, if Dr. A signs on to the system, she will only see scores related to the imaging exams that she signed. In one embodiment, the dashboard 76 is implemented in Grails, utilizing a combination of JavaScript libraries such as JQuery and D3.js to generate the graphs dynamically.

Users may specify filters 80 (shown in FIG. 3A) that influence which subset of patients are included as part of the scoring mechanism 68. In filtering module 80, users may be permitted to filter by modality, radiologist assessment (e.g., differential diagnosis or BIRADS score in this example), biopsy assessment (e.g., pathology truth diagnosis or benign/malignant in this example), and date range. However, it is appreciated that any number of filters may be incorporated.

Figure 4:
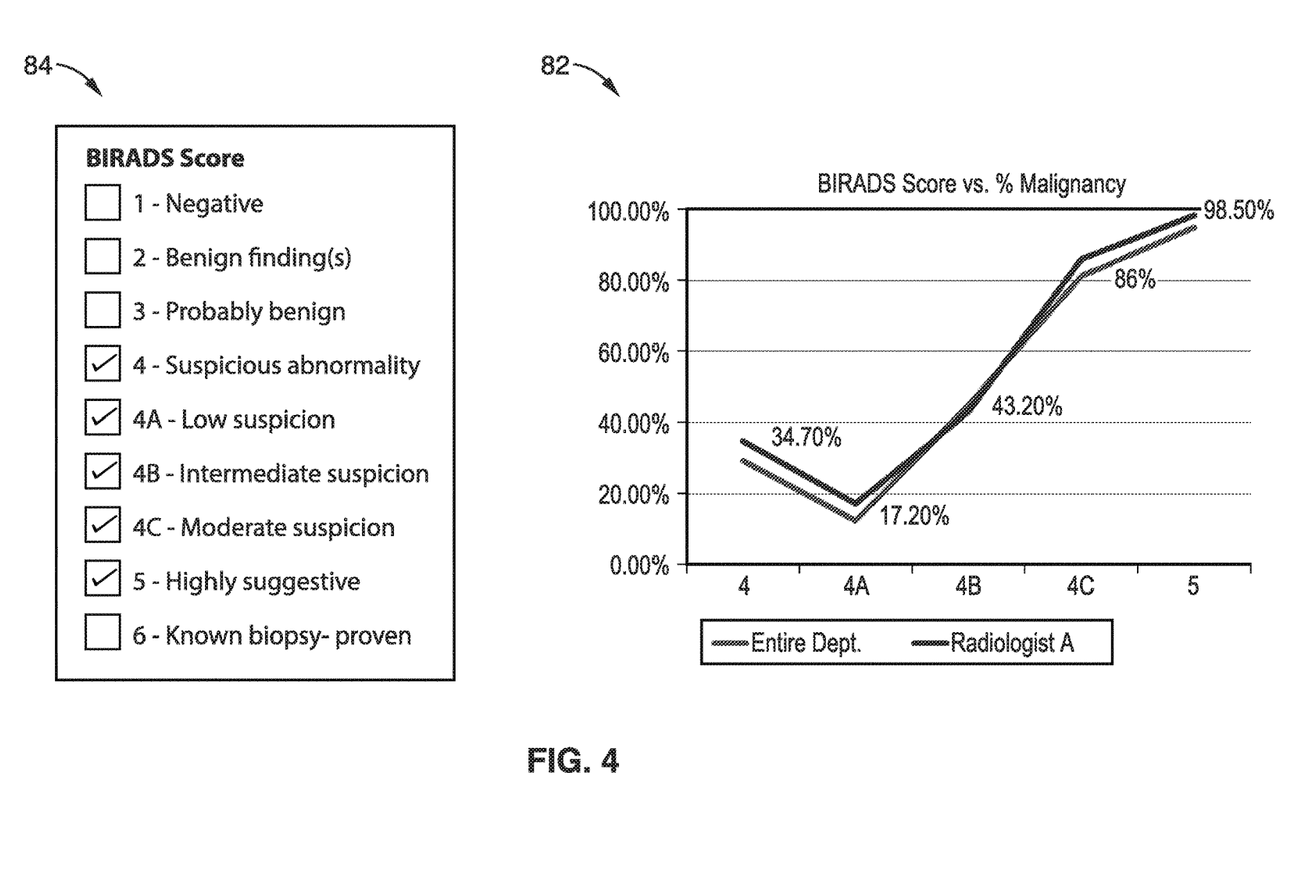
FIG. 4 shows scoring modules for the user interface dashboard.

Referring to FIG. 4, in one embodiment in which the software 40 is operating in the domain of breast cancer, the software 40 matches sentences to one of eight BIRADS categories 84; these categories can then be interpreted as being either "benign" (BIRADS 1, 2, 3) or "malignant" (BIRADS 4A, 4B, 4C, 5, 6). A corresponding output (e.g. BIRADS score vs. % malignancy) may be provided in visualization 82, also shown in FIG. 4.

The QA software 40 preferably includes code for performing one or more of the functions detailed in Table 1.

Embodiments of the present technology may be described with reference to flowchart illustrations of methods and systems according to embodiments of the technology, and/or algorithms, formulae, or other computational depictions, which may also be implemented as computer program products. In this regard, each block or step of a flowchart, and combinations of blocks (and/or steps) in a flowchart, algorithm, formula, or computational depiction can be implemented by various means, such as hardware, firmware, and/or software including one or more computer program instructions embodied in computer-readable program code logic. As will be appreciated, any such computer program instructions may be loaded onto a computer, including without limitation a general purpose computer or special purpose computer, or other programmable processing apparatus to produce a machine, such that the computer program instructions which execute on the computer or other programmable processing apparatus create means for implementing the functions specified in the block(s) of the flowchart(s).

Accordingly, blocks of the flowcharts, algorithms, formulae, or computational depictions support combinations of means for performing the specified functions, combinations of steps for performing the specified functions, and computer program instructions, such as embodied in computer-readable program code logic means, for performing the specified functions. It will also be understood that each block of the flowchart illustrations, algorithms, formulae, or computational depictions and combinations thereof described herein, can be implemented by special purpose hardware-based computer systems which perform the specified functions or steps, or combinations of special purpose hardware and computer-readable program code logic means.

Furthermore, these computer program instructions, such as embodied in computer-readable program code logic, may also be stored in a computer-readable memory that can direct a computer or other programmable processing apparatus to function in a particular manner, such that the instructions stored in the computer-readable memory produce an article of manufacture including instruction means which implement the function specified in the block(s) of the flowchart(s). The computer program instructions may also be loaded onto a computer or other programmable processing apparatus to cause a series of operational steps to be performed on the computer or other programmable processing apparatus to produce a computer-implemented process such that the instructions which execute on the computer or other programmable processing apparatus provide steps for implementing the functions specified in the block(s) of the flowchart(s), algorithm(s), formula(e), or computational depiction(s).

It will further be appreciated that the terms "programming" or "program executable" as used herein refer to one or more instructions that can be executed by a processor to perform a function as described herein. The instructions can be embodied in software, in firmware, or in a combination of software and firmware. The instructions can be stored local to the device in non-transitory media, or can be stored remotely such as on a server, or all or a portion of the instructions can be stored locally and remotely. Instructions stored remotely can be downloaded (pushed) to the device by user initiation, or automatically based on one or more factors. It will further be appreciated that as used herein, that the terms processor, computer processor, central processing unit (CPU), and computer are used synonymously to denote a device capable of executing the instructions and communicating with input/output interfaces and/or peripheral devices.

From the description herein, it will be appreciated that that the present disclosure encompasses multiple embodiments which include, but are not limited to, the following:

1. An automated system for quality control and peer review of diagnostic radiology, the system comprising: (a) a computer processor; and (b) a memory storing instructions executable on the processor; (c) the instructions, when executed, performing any one or more of the steps comprising: (i) detecting one or more diagnostic statements from natural language used in one or more of radiology reports and pathology reports; (ii) identifying a radiology diagnosis and a pathology diagnosis from the one or more diagnostic statements; (iii) matching a radiology diagnosis with a pathology diagnosis for a given patient; and (iv) characterizing the radiology diagnosis and pathology diagnosis.

2. The system of any preceding embodiment, wherein the radiology diagnosis comprises an image-derived differential diagnosis (DD).

3. The system of any preceding embodiment, wherein the pathology diagnosis comprises a truth diagnosis (TD) from a clinical data source.

4. The system of any preceding embodiment, wherein characterizing the radiology diagnosis and pathology diagnosis comprises generating one or more of the following metrics: overall concordance rate between the DD and the TD, time between imaging and biopsy relating to the DD and the TD, number of imaging studies used prior to diagnosis relating to the DD and the TD, accuracy of diagnosis for individual radiologists and modalities, and changes in concordance over time with respect to the DD and the TD.

5. The system of any preceding embodiment, wherein characterizing the radiology diagnosis and pathology diagnosis comprises evaluating concordance between the DD and the TD.

6. The system of any preceding embodiment, wherein evaluating concordance comprises generating a quality assurance (QA) score.

7. The system of any preceding embodiment, wherein detecting one or more diagnostic statements comprises identifying one or more disease categories from the one or more of radiology reports and pathology reports.

8. The system of any preceding embodiment, wherein the QA score is generated as a function of a proportion of cases where a radiologic disease categories assessment matches that of the pathology disease categories assessment from said matching.

9. The system of any preceding embodiment, wherein the QA score is computed according to the equation:

$$QA\ Score = \frac{DD \cap TD}{n};$$

wherein DD∩TD represents a number of exams where DD and TD match, and n represents a total number of pathology exams.

10. The system of any preceding embodiment, wherein radiologist recommendations (R) are also extracted from the one or more radiation reports, in addition to the differential diagnoses (DD).

11. The system of any preceding embodiment, wherein the QA score is computed according to the equation: QA Score=(DD∩TD)/n×P(TD|R); wherein P(TD|R) comprises an additional weighting term representing a probability of TD being reached within a predefined time given a radiologist's recommendation R.

12. The system of any preceding embodiment, further comprising a user platform for characterizing information content of one or more of: diagnostic reports, diagnostic accuracy, or actionable information.

13. The system of any preceding embodiment, wherein detecting one or more diagnostic statements comprising tokenizing the one or more of radiology reports and pathology reports into sections.

14. A method for automated quality control and peer review of diagnostic radiology, the method comprising: (i) detecting one or more diagnostic statements from natural language used in one or more of radiology reports and pathology reports; (ii) identifying a radiology diagnosis and a pathology diagnosis from the one or more diagnostic statements; (iii) matching a radiology diagnosis with a pathology diagnosis for a given patient; and (iv) characterizing the radiology diagnosis and pathology diagnosis; (v) wherein said method is performed by executing programming on at least one computer processor, said programming residing on a non-transitory medium readable by the computer processor.

15. The method of any preceding embodiment, wherein the radiology diagnosis comprises an image-derived differential diagnosis (DD).

16. The method of any preceding embodiment, wherein the pathology diagnosis comprises a truth diagnosis (TD) from a clinical data source.

17. The method of any preceding embodiment, wherein characterizing the radiology diagnosis and pathology diagnosis comprises generating one or more of the following metrics: overall concordance rate between the DD and the TD, time between imaging and biopsy relating to the DD and the TD, number of imaging studies used prior to diagnosis relating to the DD and the TD, accuracy of diagnosis for individual radiologists and modalities, and changes in concordance over time with respect to the DD and the TD.

18. The method of any preceding embodiment, wherein characterizing the radiology diagnosis and pathology diagnosis comprises evaluating concordance between the DD and the TD.

19. The method of any preceding embodiment, wherein evaluating concordance comprises generating a quality assurance (QA) score.

20. The method of any preceding embodiment, wherein detecting one or more diagnostic statements comprises identifying one or more disease categories from the one or more of radiology reports and pathology reports.

21. The method of any preceding embodiment, wherein the QA score is generated as a function of a proportion of cases where a radiologic disease categories assessment matches that of the pathology disease categories assessment from said matching.

22. The method of any preceding embodiment, wherein the QA score is computed according to the equation:

$$QA\ Score = \frac{DD \cap TD}{n};$$

wherein DD∩TD represents a number of exams whether DD and TD match, and n represents a total number of pathology exams.

23. The method of any preceding embodiment, wherein radiologist recommendations (R) are also extracted from the one or more radiation reports, in addition to the differential diagnoses (DD).

24. The method of any preceding embodiment, wherein the QA score is computed according to the equation: QA Score=(DD∩TD)/n×P(TD|R); wherein P(TD|R) comprises an additional weighting term representing a probability of TD being reached within a predefined time given a radiologist's recommendation R.

25. The method of any preceding embodiment, further comprising: characterizing on a user platform information content of one or more of: diagnostic reports, diagnostic accuracy, or actionable information.

26. The method of any preceding embodiment, wherein detecting one or more diagnostic statements comprises tokenizing the one or more of radiology reports and pathology reports into sections.

27. A system for quality control and peer review of diagnostic radiology, the system comprising: (a) a computer processor; and (b) a memory storing instructions executable on the processor; (c) the instructions, when executed, performing any one or more of the steps comprising: (i) for a given patient in a cohort, locating a report (T) that contains a "truth" or "gold standard" diagnosis (TD) for a disease of interest; (ii) for all diagnostic radiology reports related to the disease of interest preceding T, using informatics tools to extract the differential diagnoses (DD) and recommendations (R) provided by a radiologist; and (iii) computing a QA score by comparing over time differential diagnoses in DD to the true diagnosis, TD.

28. The method of any preceding embodiment, wherein the QA score is computed according to the equation:

$$QA\ Score = \frac{DD \cap TD}{n};$$

wherein where DD∩TD represents a number of exams whether DD and TD match, and n represents a total number of pathology exams.

29. The method of any preceding embodiment, further comprising: optionally weighting the score by radiologist recommendations, R.

30. The method of any preceding embodiment, wherein the QA score is computed according to the equation: QA Score=(DD∩TD)/n×P(TD|R); wherein where DD∩TD represents a number of exams whether DD and TD match, and n represents a total number of pathology exams; and wherein P(TD|R) comprises an additional weighting term representing a probability of TD being reached within a predefined time given a radiologist's recommendation R.

Although the description herein contains many details, these should not be construed as limiting the scope of the disclosure but as merely providing illustrations of some of the presently preferred embodiments. Therefore, it will be appreciated that the scope of the disclosure fully encompasses other embodiments which may become obvious to those skilled in the art.

In the claims, reference to an element in the singular is not intended to mean "one and only one" unless explicitly so stated, but rather "one or more." All structural, chemical, and functional equivalents to the elements of the disclosed embodiments that are known to those of ordinary skill in the art are expressly incorporated herein by reference and are intended to be encompassed by the present claims. Furthermore, no element, component, or method step in the present disclosure is intended to be dedicated to the public regardless of whether the element, component, or method step is explicitly recited in the claims. No claim element herein is to be construed as a "means plus function" element unless the element is expressly recited using the phrase "means for". No claim element herein is to be construed as a "step plus function" element unless the element is expressly recited using the phrase "step for".

TABLE 1

| Functions of QA Software Code | | |
|---|---|---|
| Function Name | Description | Inputs & Outputs |
| selectBiopsies(cpis) | Retrieve information from biopsy table based on input parameters | cpis(ControlPanelItems): web form parameters<br>biopsies(list): biopsies |
| selectRadiologyEx (cpis) | Retrieve information from the radiology table based on input parameters | cpis(ControlPanelItems): web form parameters<br>radiologyEx(list): radiology exams |
| selectAllRadiologyEx ByPatientId(pList, cpis) | Retrieve information from the radiology table based on patient id list | pList(list): patient IDs<br>radiologyEx(list): radiology exams |

TABLE 1-continued

Functions of QA Software Code

| Function Name | Description | Inputs & Outputs |
| --- | --- | --- |
| selectMinBiopsyDate (dCol) | Wrapper function to select minimum date in biopsy table | dCol(string): name of the date column<br>result(string): value of the minimum date |
| selectMaxBiopsyDate (dCol) | Wrapper function to select maximum date in biopsy table | dCol(string): name of the date column<br>result(string): value of the maximum date |
| singleRadiologyProj (proj, col) | Using GORM projection to select a desired value from a column in the radiology table | proj(string): the projection<br>col(string): column name<br>result(string): value of the projection |
| selectDistinct(grails Application, domain Name, column) | Select distinct values from a column in a table | grailsApplication(GrailsApplication): provides access to metadata, config, etc<br>domainName(string): name of table<br>column(string): name of column<br>result(list): distinct values |
| selectDistinctWithCount (grailsApplication, domainName, column) | Select distinct values and associated counts from a column in a table | grailsApplication(GrailsApplication): provides access to metadata, config, etc<br>domainName(string): name of table<br>columns(list): name of columns<br>result(list): distinct values |
| selectDistinctM(grails Application, domain Name, columns) | Select distinct terms from multiple columns in a table | grailsApplication(GrailsApplication): provides access to metadata, config, etc<br>domainName(string): name of table<br>result(int): the count |
| selectByProp(grails Application, domain Name, props) | Generic retrieval mechanism to retrieve information from a table given some properties and values | grailsApplication(GrailsApplication): provides access to metadata, config, etc<br>domainName(string): name of table<br>class(Class): class object |
| aToB(_a) | Map radiologist assessment to a categorical score | _a(string): assessment<br>result(string): birad score |
| bListToAList(_bList) | Convert a list of categorical scores to radiologist assessments | _aList(list): assessments<br>result(list): birad scores |
| _mapToList(tempMap) | Convert keys in a map to a sorted list | _bList(list): birad scores<br>result(list): assessments<br>tempMap(map): a map<br>tempList(list): sorted list |
| getRadiologist(_radiologist) | Convert a single _radiologist to a radiologist object | _radiologist(list): last, first, and middle name<br>radiologist(Radiologist): contains display name and value used in the web form |
| remodelRadiologist (_radiologistList) | Convert a list of _radiologist to a list of radiologist objects | _radiologistList(list): each item is a _radiologist<br>radiologistList(list): each item is a Radiologist |
| getRadiologistName (user, val) | Based on the user and the radiologist selected in the web form, return a display name | user(User): spring security current user object<br>val(string): the selected radiologist in the web form<br>name(string): display name |
| getObjMap(obj, prop) | Given a list of objects, group them by the value of a property 'prop' | obj(list): list of objects with property 'prop'<br>prop(string): property name<br>objMap(map): key: value of property 'prop', value: list of objects where the value of property 'prop' is the key |
| paramsToCpis(cpis, p) | Update the Control Panel Items with values from the submitted form | cpis(ControlPanelItems): web form parameters<br>p(Params): grails object of request parameters |

TABLE 1-continued

Functions of QA Software Code

| Function Name | Description | Inputs & Outputs |
| --- | --- | --- |
| getBreakdown(objMap) | For each item in an objMap where the value is a list, calculate its frequency (percentage) in relation to all items in the objMap | objMap(map): key: value of property 'prop', value: list of objects where the value of property 'prop' is the key results(list): each item is a map consisting of name, count, proportion in decimals, and % for the corresponding value in the objMap |
| getBreakdown(objList) | For each item in an objList, calculate the proportion in relation to all items in the objList | objList(list): each item is a map where the key: value of property 'prop', value: count results(list): each item is a map consisting of name, count, proportion in decimals, and % for the corresponding item in the objList |
| getPieChartJSON(obj) | Takes results and reformats them using JSON as an input in to the pie chart generation method | obj(list): results from getBreakdown someList(JSON): the list converted to JSON |
| getSBList(bMap, rMap) | Generate a list of biopsies that belong to patients who have both pathology and radiology diagnoses | bMap(map): key: 'patientId', value: list of biopsies for a patient with patientId 'patientId' rMap(map): key: 'patientId', value: list of radiology exams for a patient with patient Id 'patientId' |
| getSRList(bMap, rMap) | Generate a list of radiology exams that belong to patients who have both pathology and radiology diagnoses | bMap(map): key: 'patientId', value: list of biopsies for a patient with patientId 'patientId' rMap(map): key: 'patientId', value: list of radiology exams for a patient with patientId 'patientId' sRList(list): radiology exams |
| getProfileStackValues (biopVsRadObj) | Generate a map of JSON objects for stacked bar chart method | biopVsRadObj(map): see getBiopVsRad stackValues(map): key: radiologist display name, value: 2D array as JSON |
| getModVsLesClass (biopVsRadObj) | Generate a 2D array for stacked bar chart method | biopVsRadObj(map): see getBiopVsRad result(2D array): matrix of values and labels |
| stackToPie(objJSON) | Turns stacked bar chart data as JSON into a map of pie chart data as JSON | objJSON(JSON): the value of an item from stackValues biradMap(map): key: birad score, value: pie chart data as JSON |
| getDateBinData(d1, d2, dType, cpis, sPairs, rAssess) | Generate data used to draw radiology categorical assessment over time as a stacked bar chart | d1(Date): date lower bound d2(Date): date upper bound dType(string): time bin size (YEAR/MONTH/etc) cpis(ControlPanelItems): web form parameters sPairs(map): key: radiologist display name, value: list where each item is a list of matching biopsy and radiology reports rAssess(list): selected birad scores from the web form dateBinData(map): key: radiologist display name, value: 2D array of values and labels |
| getBin(d1, d2, type) | Generate bins between two given dates | d1(Date): date lower bound d2(Date): date upper bound type(string): time bin size (YEAR/MONTH/etc) bin(map): key: bin label (2007/2008 or 2010-05/2010-06 etc), value: 0 |

TABLE 1-continued

Functions of QA Software Code

| Function Name | Description | Inputs & Outputs |
| --- | --- | --- |
| dateToGregorianCalendar (dateObj) | Convert a Date object to a GregorianCalendar object | dateObj(Date): a Date object gc(GregorianCalendar): a GregorianCalendar object |
| getJSONPerKey(obj) | Convert the values of a map to JSON objects | obj(map): key: some key, value: some data structure JSONObj(map): key some key, value: some data structure as JSON |
| getDisplayName(r) | Turn list of last, first, and middle name to display name | r(list): last, first, and middle name displayName(string): radiologist display name |
| getItemValue(r) | Turn list of last, first, and middle name to web form item value | r(list): last, first, and middle name itemValue(string): web form item value |
| getBiopVsRad(bMap, rMap, cpis, params, rAssess) | Iterates through pathology and radiology exams to find matching reports and captures other statistics while performing the match | bMap(map): key: 'patientId', value: list of biopsies for a patient with patientId 'patientId' rMap(map): key: 'patientId', value: list of radiology exams for a patient with patientId 'patientId' cpis(ControlPanelItems): web form parameters params(Params): grails object of request parameters rAssess(list): selected birad scores from the web form biopVsRadObj(map): count of birad scores/biopsy results, list of patients who have matching exams, list of patients without matching exams, reasons exams do not match and how many, number of matching pairs (total and per radiologist), time between the radiology and biopsy reports for matching pairs, average time between radiology and biopsy for matching pairs, matching pairs grouped by the radiologist, earliest radiology report date, latest radiology report date |
| dateMatch(b, r, dCol) | Checks that radiology date is before biopsy date | b(Biopsy): biopsy report r(Radiology): radiology report dCol(string): date column |
| sideMatch(b, r) | Checks that information from the radiology side matches that of the pathology side | b(Biopsy): biopsy report r(Radiology): radiology report |
| modalityMatch(rModality, r, fMap) | Check if radiologist match | r(Radiology): radiology report fMap(map): key: reason for non-match, value: count rModality(list): selected modalities from the web form |
| biradVsMalignancy (biopVsRadObj) | Get data for radiology categorical assessment versus pathology assessment | r(Radiology): radiology report fMap(map): key: reason for non-match, value: count |
| radiologistScore(biop VsRadObj) | Calculate radiologist's performance, comparing radiology categorical assessment against pathology assessment | rAssessmentDesc(list): selected birad scores from the web form r(Radiology): radiology report fMap(map): key: reason for non-match, value: count |
| getRadiologistName (r) | Get the radiologist display name | biopVsRadObj(map): see getBiopVsRad biradVsM(map): key: radiologist display name, value: 2D array of values |
| radBiopCounts(rVs BMap, rName, birad, lesionClassDesc, rAssess) | Keep track of radiologist's categorical assessment count | biopVsRadObj(map): see getBiopVsRad score(map): contains % correct for each birad score and total for each radiologist |

TABLE 1-continued

Functions of QA Software Code

| Function Name | Description | Inputs & Outputs |
| --- | --- | --- |
| adAuth(uid, password) | Authenticate user against single sign on login system | uid(string): AD username<br>password(string): AD password<br>auth(AuthObj): authorization object containing login status and status message |
| authObj(resp) | Parses the single sign on login system response and keep track of relevant info | resp(string): response XML<br>auth(AuthObj): authorization object containing login status and status message |

What is claimed is:

1. An automated system for quality control and peer review of diagnostic radiology, the system comprising:
   (a) a computer processor; and
   (b) a memory storing instructions executable on the processor;
   (c) the instructions, when executed, performing the steps comprising:
      (i) detecting one or more diagnostic statements from natural language used in one or more of radiology reports and pathology reports;
      (ii) identifying a radiology diagnosis comprising an image-derived differential diagnosis (DD) and a pathology diagnosis comprising a truth diagnosis (TD) from the one or more diagnostic statements in a clinical data source;
      (iii) matching a radiology diagnosis with a pathology diagnosis for a given patient;
      (iv) characterizing the radiology diagnosis and pathology diagnosis; and
      (v) outputting a quality assurance (QA) score;
      (vi) wherein radiologist recommendations (R) are also extracted from the one or more radiology reports, in addition to the differential diagnoses (DD)
      (vii) wherein the QA score is computed according to the equation:

$$QA\ Score=(DD \cap TD)/n \times P(TD|R);\ \text{and}$$

(viii) wherein DD∩TD represents a number of exams where DD and TD match, n represents a total number of pathology exams greater than 1, and P(TD|R) comprises an additional weighting term representing a probability of TD being reached within a predefined time given a radiologist's recommendation R.

2. The system of claim 1, wherein characterizing the radiology diagnosis and pathology diagnosis comprises generating one or more of the following metrics: overall concordance rate between the DD and the TD, time between imaging and biopsy relating to the DD and the TD, number of imaging studies used prior to diagnosis relating to the DD and the TD, accuracy of diagnosis for individual radiologists and modalities, and changes in concordance over time with respect to the DD and the TD.

3. The system of claim 2, wherein detecting one or more diagnostic statements comprises identifying one or more disease categories from the one or more of radiology reports and pathology reports.

4. The system of claim 3, wherein the QA score is generated as a function of a proportion of cases where a radiologic disease categories assessment matches that of the pathology disease categories assessment from said matching.

5. The system of claim 1, further comprising a user platform for characterizing information content of one or more of: diagnostic reports, diagnostic accuracy, or actionable information.

6. The system of claim 1, wherein detecting one or more diagnostic statements comprises tokenizing the one or more of radiology reports and pathology reports into sections.

7. A method for automated quality control and peer review of diagnostic radiology, the method comprising:
   (i) detecting one or more diagnostic statements from natural language used in one or more of radiology reports and pathology reports;
   (ii) identifying a radiology diagnosis comprising an image-derived differential diagnosis (DD) and a pathology diagnosis comprising a truth diagnosis (TD) from the one or more diagnostic statements in a clinical data source;
   (iii) matching a radiology diagnosis with a pathology diagnosis for a given patient; and
   (iv) characterizing the radiology diagnosis and pathology diagnosis;
   (v) outputting a quality assurance (QA) score;
   (vi) wherein radiologist recommendations (R) are also extracted from the one or more radiology reports, in addition to the differential diagnoses (DD);
   (vii) wherein the QA score is computed according to the equation:

$$QA\ Score=(DD \cap TD)/n \times P(TD|R);\ \text{and}$$

(viii) wherein DD∩TD represents a number of exams where DD and TD match, n represents a total number of pathology exams greater than 1, and P(TD|R) comprises an additional weighting term representing a probability of TD being reached within a predefined time given a radiologist's recommendation R; and
      (ix) wherein said method is performed by executing programming on at least one computer processor, said programming residing on a non-transitory medium readable by the computer processor.

8. The method of claim 7, wherein characterizing the radiology diagnosis and pathology diagnosis comprises generating one or more of the following metrics: overall concordance rate between the DD and the TD, time between imaging and biopsy relating to the DD and the TD, number of imaging studies used prior to diagnosis relating to the DD and the TD, accuracy of diagnosis for individual radiologists and modalities, and changes in concordance over time with respect to the DD and the TD.

9. The method of claim 7, wherein detecting one or more diagnostic statements comprises identifying one or more disease categories from the one or more of radiology reports and pathology reports.

10. The method of claim 9, wherein the QA score is generated as a function of a proportion of cases where a radiologic disease categories assessment matches that of the pathology disease categories assessment from said matching.

11. The method of claim 7, further comprising:
characterizing on a user platform information content of one or more of: diagnostic reports, diagnostic accuracy, or actionable information.

12. The method of claim 7, wherein detecting one or more diagnostic statements comprises tokenizing the one or more of radiology reports and pathology reports into sections.

13. A system for quality control and peer review of diagnostic radiology, the system comprising:
 (a) a computer processor; and
 (b) a memory storing instructions executable on the processor;
 (c) the instructions, when executed, performing the steps comprising:
 (i) for a given patient in a cohort, locating a report (T) that contains a "truth" or "gold standard" diagnosis (TD) for a disease of interest;
 (ii) for all diagnostic radiology reports related to the disease of interest preceding T, using informatics tools to extract the differential diagnoses (DD) and recommendations (R) provided by a radiologist; and
 (iii) outputting a quality assurance (QA) QA score by comparing over time differential diagnoses in DD to the true diagnosis, TD;
 (iv) wherein radiologist recommendations (R) are also extracted from the one or more radiology reports, in addition to the differential diagnoses (DD);
 (vii) wherein the QA score is computed according to the equation:

QA Score=$(DD \cap TD)/n \times P(TD|R)$; and (viii) wherein $DD \cap TD$ represents a number of exams where DD and TD match, n represents a total number of pathology exams greater than 1, and P(TD|R) comprises an additional weighting term representing a probability of TD being reached within a predefined time given a radiologist's recommendation R.

* * * * *